(12) United States Patent
Nomoto et al.

(10) Patent No.: US 7,700,336 B2
(45) Date of Patent: Apr. 20, 2010

(54) LECITHINIZED SUPEROXIDE DISMUTASE COMPOSITION AND A PROCESS FOR ITS PRODUCTION

(75) Inventors: Hideo Nomoto, Yokohama (JP);
Toshiaki Nakayama, Yokohama (JP);
Maki Murahashi, Ichihara (JP);
Yoshitomi Morizawa, Yokohama (JP)

(73) Assignees: LTT Bio-Pharma Co., Ltd., Tokyo (JP);
Beijing Tide Pharmaceutical Co., Ltd., Beijing (CN)

( * ) Notice: Subject to any disclaimer, the term of this patent is extended or adjusted under 35 U.S.C. 154(b) by 338 days.

(21) Appl. No.: 11/733,989

(22) Filed: Apr. 11, 2007

(65) Prior Publication Data

US 2007/0178080 A1  Aug. 2, 2007

Related U.S. Application Data

(63) Continuation of application No. PCT/JP2005/018454, filed on Oct. 5, 2005.

(30) Foreign Application Priority Data

Oct. 12, 2004 (JP) .............................. 2004-297519

(51) Int. Cl.
*C12N 9/02* (2006.01)
(52) U.S. Cl. ...................... 435/189; 435/183; 424/94.4; 424/94.3; 424/94.1
(58) Field of Classification Search ................ 435/189, 435/183; 424/94.4, 94.3, 94.1
See application file for complete search history.

(56) References Cited

U.S. PATENT DOCUMENTS

| 5,109,118 A | 4/1992 | Mizushima |
| 5,310,958 A | 5/1994 | Mizushima |
| 5,362,491 A | 11/1994 | Mizushima |
| 5,762,929 A | 6/1998 | Kinoshita et al. |

FOREIGN PATENT DOCUMENTS

| EP | 1 188 445 A1 | 3/2002 |
| JP | 2-62829 | 3/1990 |
| JP | 9-110717 | 4/1997 |
| JP | 9-117279 | 5/1997 |
| JP | 117279 A1 * | 5/1997 |
| JP | 3070980 | 5/2000 |

OTHER PUBLICATIONS

Derwent machine translation of JP117279A1 downloaded May 26, 2003.*
Hangaishi et al., Biochem. Biophys. Res. Commun., 2001, vol. 285, No. 5, pp. 1220-1225.
Wagner et al, Eur. J. Pharm. Biopharm., 2002, vol. 54, No. 2, pp. 213-219.
R. Igarashi, et al., "Lecithinization of Superoxide Dismutase Potentiates Its Protective Effect against Forssman Antiserum-Induced Elevation in Guinea Pig Airway Resistance", The Journal of Pharmacology and Experimental Therapeutics, XP009108879, 1992, vol. 262, No. 3, pp. 1214-1219.
R. Igarashi, et al., "Lecithinized Superoxide Dismutase Enhances Its Pharmacologic Potency by Increasing Its Cell Membrane Affinity", The Journal of Pharmacology and Experimental Therapeutics, American Society for Pharmacology and Experimental Therapeutics, XP009031309, Jan. 1, 1994, vol. 271, No. 3, pp. 1672-1677.
Yusuke Hori, et al., "Effect of Lecithinized-Superoxide Dismutase on the Rat Colitis Model Induced by Dextran Sulfate Sodium", Japanese Journal of Pharmacology, JPTHE Japanese Pharmacological Society, Kyoto, XP009030058, Jan. 1, 1997, vol. 74, No. 1, pp. 99-103.

* cited by examiner

*Primary Examiner*—Irene Marx
*Assistant Examiner*—Susan Hanley
(74) *Attorney, Agent, or Firm*—Oblon, Spivak, McClelland, Maier & Neustadt, L.L.P.

(57) ABSTRACT

To provide a lecithinized superoxide dismutase (PC-SOD) composition useful as a drug material and a process for its production. The PC-SOD composition contains a PC-SOD obtained by substituting at least amino group in a specific SOD with a lecithin moiety represented by the following formula (I), wherein the PC-SOD contains a PC-SOD (A) having an m number of amino groups substituted with the lecithin moieties (wherein m is an integer of from 1 to 4 and averages from 1.5 to 2.4 as a main component and the PC-SOD (A) consists of a PC-SOD (a1) wherein m=1, a PC-SOD (a2) wherein m=2, a PC-SOD (a3) wherein m=3 and a PC-SOD (a4) wherein m=4.

8 Claims, No Drawings

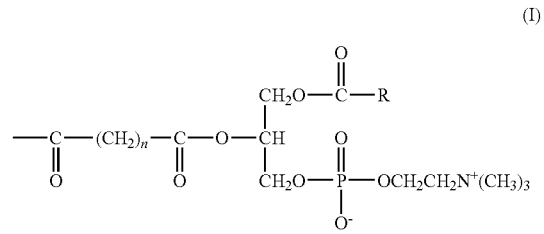

LECITHINIZED SUPEROXIDE DISMUTASE COMPOSITION AND A PROCESS FOR ITS PRODUCTION

CROSS-REFERENCE TO A RELATED APPLICATION

The present application is a continuation of International Application PCT/JP05/018454, filed Oct. 5, 2005, which claims priority to Japanese Application No. 2004-297519, filed Oct. 12, 2004.

TECHNICAL FIELD

The present invention relates to a lecithinized superoxide dismutase composition and a process for its production.

BACKGROUND ART

Superoxide dismutases (hereinafter referred to simply as SODs) are enzymes present in a wide variety of organisms such as animals, plants and microorganisms. SODs catalyze disproportionation of the free reactive oxygen species called the superoxide anion radical. SODs are expected to be used as an antirheumatic drug, as a therapeutic agent for autoimmune diseases and myocardial infarction, during organ transplantation, for scavenging radicals generated in vivo by the use of antithrombotic agents after cerebral infarction, and for various kinds of inflammation (non-patent document 1).

Various SOD derivatives have been proposed. For example, a lecithinized superoxide dismutase (hereinafter lecithinized superoxide dismutase will be referred to as PC-SOD) with greatly improved accumulability in target lesions and greatly improved in vivo stability obtained by lecithinizing a specific SOD is proposed as a drug (patent document 1).

Patent Document 1: Japanese Patent No. 3070980

Non-patent Document 1: "Kasseisanso-no Rinsho-heno Tembo (Clinical Review of Active Oxygen)", edited by Naoyuki Taniguchi, published by Iyaku Journal Co., Ltd., Tokyo, pp.61-111 (1994)

DISCLOSURE OF THE INVENTION

The Problems that the Invention is to Solve

However, practical medicinal use of the PC-SOD has some problems. For example, the PC-SOD obtained conventionally by reacting a specific SOD with a lecithin derivative has a problem of instable enzymatic activity which may cause trouble when or after it is formulated into preparations. Besides, it is not obtained in sufficiently high yields by the conventional process.

The object of the present invention is to provide a PC-SOD composition with good stability which is useful as a drug material.

Means of Solving the Problems

As a result of their extensive research, the present inventors found that a PC-SOD composition containing a PC-SOD (A) obtained by substituting from 1 to 4 amino groups in a specific SOD with lecithin moieties (hereinafter referred to as PC-SOD (A)) as a main component solves the above-mentioned problems. Further, they studied the conditions for production of the PC-SOD composition and found that the PC-SOD composition is obtainable in high yields by reacting a lecithin derivative with a specific SOD in a specific ratio and isolating the reaction product by a specific process.

Namely, the present invention provides a PC-SOD composition containing a PC-SOD obtained by substituting at least one amino group in copper- and/or zinc-coordinated human superoxide dismutase having a hydroxyethylthio group instead of the mercapto group in cysteine at the position 111, with at least one lecithin moiety represented by the following formula (I):

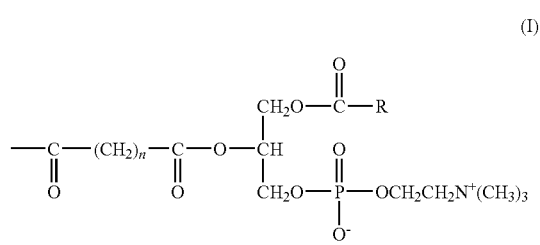

(wherein R is a $C_{8-30}$ alkyl group, and n is an integer of from 2 to 10), wherein the PC-SOD comprises a PC-SOD (A) having an m number of amino groups substituted with the lecithin moieties (wherein m is an integer of from 1 to 4 and averages from 1.5 to 2.4) as a main component, and the PC-SOD (A) consists of from 25 to 40 mol % of a lecithinized superoxide dismutase (a1) wherein m=1, from 35 to 50 mol % of a lecithinized superoxide dismutase (a2) wherein m=2, from 10 to 20 mol % of a lecithinized superoxide dismutase (a3) wherein m=3 and from 5 to 15 mol % of a lecithinized superoxide dismutase (a4) wherein m=4.

The present invention also provides a process for producing the lecithinized superoxide dismutase composition as defined in any one of claims 1 to 7, which comprises a lecithinizing step of reacting a lecithin derivative represented by the following formula (III):

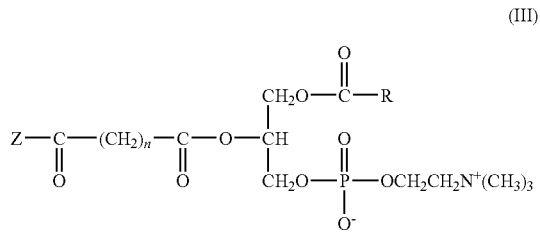

(wherein R is a $C_{8-30}$ alkyl group, Z is a hydroxyl group or an active ester-forming group eliminating a carbonyl group, and n is an integer of from 2 to 10) with from 0.05 to 0.4 time as many moles of copper- and/or zinc-coordinated human superoxide dismutase having a hydroxyethylthio group instead of the mercapto group in cysteine at the position 111 to obtain a crude PC-SOD, and a purifying step of purify the crude PC-SOD by ion exchange column chromatography.

Effects of the Invention

The PC-SOD composition of the present invention has a stable enzymatic activity and a high in vivo stability and is easy to formulate into a preparation. Therefore, it is useful as a drug material. The process of the present invention gives the PC-SOD composition in high yields.

Best Mode of Carrying Out the Invention

The PC-SOD composition of the present invention contains a PC-SOD having a structure of copper- and/or zinc-coordinated human superoxide dismutase (hereinafter referred to as human SOD) which has a hydroxyethylthio group instead of the mercapto group in cysteine at the position 111 and has at least one amino group substituted with a lecithin moiety represented by the following formula (I).

The SOD used for producing the PC-SOD may be obtained by any method without particular restrictions and may be of human origin or other origin. Namely, the human SOD may be of any origin as long as it has the same structure as the SOD of human origin.

In the present invention, the PC-SOD consists of a PC-SOD (A) which will be described later and a PC-SOD (B) (hereinafter referred to as PC-SOD(B)) obtained by substituting at least 5 amino groups in human SOD with lecithin moieties (I). The total of PC-SODs means the sum of the PC-SOD (A) and the PC-SOD (B).

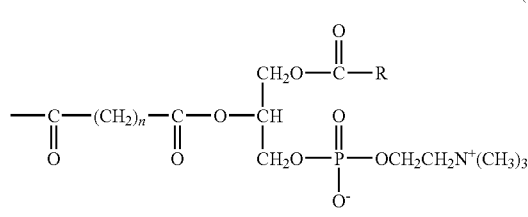

(I)

In the lecithin moiety represented by the formula (I) (hereinafter referred to as the lecithin moiety (I)), R is a $C_{8-30}$ alkyl group, preferably a $C_{14-22}$ alkyl group. R may be linear or branched, preferably linear. R is preferably a linear alkyl group having 13, 15 or 17 carbon atoms, particularly a linear $C_{15}$ alkyl group.

n is an integer of from 2 to 10, preferably from 2 to 6, particularly preferably 3.

In the present invention, the PC-SOD in the PC-SOD composition generically refers to compounds obtained by substituting at least one amino group in human SOD with a lecithin moiety. Because human SOD has 12 amino groups, the PC-SOD has from 1 to 12 lecithin moieties (I).

"Substituted with a lecithin moiety (I)" means that either hydrogen atom in an amino group ($-NH_2$) is replaced by a lecithin moiety.

The PC-SOD composition of the present invention contains a PC-SOD (A) wherein the number (m) of lecithin moieties (I) is an integer of from 1 to 4, and the average of m is from 1.5 to 2.4, as a main component m is the number of lecithin moieties on amino groups in the PC-SOD (A). "Containing the PC-SOD (A) as a main component" means that among PC-SODs in the PC-SOD composition, the PC-SOD (A) constitutes the largest proportion. The ratio of the PC-SOD (A) to the total of PC-SODs is preferably at least 75 mass%, particularly from 85 to 100 mass %.

Further, in the present invention, the PC-SOD (A) contains four types of PC-SOD wherein m is 1, 2, 3 and 4, in specific ratios, respectively. Namely, the PC-SOD (A) consists of from 25 to 40 mol % of a PC-SOD (a1) wherein m=1, from 35 to 50 mol % of a PC-SOD (a2) wherein m=2, from 10 to 20 mol % of a PC-SOD (a3) wherein m=3 and from 5 to 15 mol % of a PC-SOD (a4) wherein m=4.

The average of m is from 1.5 to 2.4. The average of m is calculated on a molar basis from the molar ratios of the PC-SODs (a1), (a2), (a3) and (a4) to the total amount.

When the number of lecithin moieties bound to the PC-SOD is large, the PC-SOD is highly hydrophobic, and hence adherent to cells and readily absorbed by adipose tissues. On the other hand, when the number of lecithin moieties bound to the PC-SOD is small, the PC-SOD is hydrophilic and readily applicable to aqueous preparations such as injections and has other advantages are that it has a high enzymatic activity and that it is less likely to be recognized as an antigen in vivo.

When the PC-SOD is formulated into a preparation, it is necessary that the in vivo dynamics, stability and ease of formulation are well-balanced. In view of these factors, the present inventors found that the optimum average number of lecithin moieties (I) bound to the PC-SOD is from 1.5 to 2.4. They also found that in view of the stability of the PC-SOD composition of the present invention, it is not enough that the PC-SOD has from 1.5 to 2.4 lecithin moieties on average, and that the presence of both of a PC-SOD having a moderate number of lecithin moieties (I) and a PC-SOD having less lecithin moieties (I) leads to improved stability as a drug material and is effective for production of a drug material and a preparation.

The PC-SOD composition of the present invention may contain, in addition to the PC-SOD (A), a PC-SOD (B).

The number (r) of lecithin moieties (I) in the PC-SOD (B) is from 5 to 12.

Because amino groups inside the PC-SOD conformation are resistant to substitution, in general, r is preferably from 5 to 8.

When the PC-SOD composition contains the PC-SOD (B), the amount of the C-SOD (B) is preferably at most 25 mass %, particularly at most 15 mass %, based on the total PC-SOD in the PC-SOD composition. If it exceeds 25 mass %, the effects of the present invention may be ruined for the above-mentioned reasons.

In the present invention, the PC-SOD which is a compound obtained substituting at least one amino group in human SOD with a lecithin moiety (I) may have at least one amino group substituted with a moiety other than the lecithin moiety (I), such as a group obtained by partially decomposition of a lecithin moiety (I) or a decomposition product of the lecithin derivative used for synthesis of the PC-SOD as a substituent on an amino group.

Specific examples of such a group other than the lecithin moiety (I) include the following groups, wherein n is the same as defined for the lecithin moiety (I).

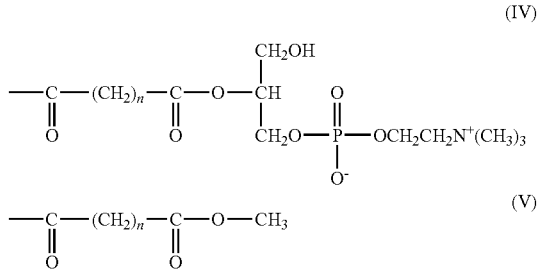

-continued

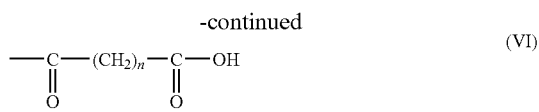

(VI)

Meanwhile, the concept of the PC-SOD in the present invention does not cover a compound which is a PC-SOD having no amino groups substituted with a lecithin moiety (I) and having amino groups substituted with groups other than the lecithin moiety (I) such as the above-mentioned groups (IV) to (VI).

It is preferred to control the ratio of the PC-SOD (A) in the PC-SOD composition of the present invention from various viewpoints.

For example, the ratio of the PC-SOD (A) measured by high performance liquid chromatography (hereinafter referred to as HPLC) is preferably at least 85%, more preferably from 85 to 100%, particularly from 90 to 100% (in terms of peak area in the chromatogram).

The ratio of the PC-SOD (A) measured by sodium dodecyl sulfate-polyacrylamide gel electrophoresis is preferably at least 80%, particularly from 85 to 100% (in terms of peak area in the chromatogram).

The measurement conditions described later in the Examples may be used for HPLC and sodium dodecyl sulfate-polyacrylamide gel electrophoresis.

When the ratio of the PC-SOD (A) is controlled within the above-mentioned range, it is possible to steadily obtain a PC-SOD composition with stable enzymatic activity and high in vivo stability. The above-mentioned analytical techniques afford more effective control. The resulting PC-SOD composition is highly stable and easy to formulate into preparations.

The PC-SOD composition of the present invention preferably contains the PC-SOD (A) as a main component in the form of a dimer of PC-SOD (A) which are the same or different in m, to exhibit its enzymatic activity sufficiently. The dimer may be formed, for example, from two molecules of the PC-SOD (a2) or from one molecule of the PC-SOD (a1) and one molecule of the PC-SOD (a3).

When the PC-SOD contains the PC-SOD (B), the PC-SOD (B) may form a dimer with the PC-SOD (A) and/or by itself.

The PC-SOD composition of the present invention may contain compounds other than the PC-SOD (A) and the PC-SOD (B) (hereinafter referred to as additional compounds).

As an additional compound, a fatty acid represented by the following formula (II) may be mentioned:

RCOOH     (II)

[wherein R is the same as defined above for R in the formula (I)].

The amount of the fatty acid represented by the formula (II) is preferably from 0.01 to 0.15 nmol per 1 mg of the total of PC-SODs.

The fatty acid in the PC-SOD composition may be measured by gas chromatography, HPLC, mass spectrometry or other techniques. It may be measured by HPLC after labeled with a labeling reagent. When the PC-SOD composition has a low fatty acid concentration, it is preferred to use a labeling reagent.

An additional compound may be a compound which is human SOD having no amino group substituted with a lecithin moiety (I) and at least one amino group substituted with at lease one of the above-mentioned groups represented by the formulae (IV), (V) and (VI).

The amount of, if any, additional compounds in the PC-SOD composition of the present invention measured by sodium dodecyl sulfate-polyacrylamide gel electrophoresis is preferably at most 20%, particularly from 0 to 15% (in terms of peak area in the chromatogram).

The PC-SOD composition of the present invention has a superoxide dismutase activity (SOD activity). The SOD activity is preferably measured as a specific activity in relation to that of the unlecithinized SOD, i.e., human SOD.

Among the methods for measurement of the specific activity of the PC-SOD composition such as the cytochrome C method, the nitro blue-tetrazolium method, the epinephrine method and the nitrite method, it is preferred to measure the specific activity by the cytochrome method. The specific activity can be measured by the cytochrome C method as described by Y. Oyanagi (SOD and active oxygen regulators, p.95(1989), J. M. McCord (J. Biol. Chem., Vol.224, p.6049 (1969) and K. Asada (Agr. Biol. Chem., Vol.38, p.471(1974)).

The PC-SOD composition of the present invention preferably has a specific activity of at least 2000 units, particularly from 2300 to 7000 units, per 1 mg of the total of PC-SODs, measured by the cytochrome C method, in view of ease of formulation, in vivo stability and efficacy.

The PC-SOD composition of the present invention is obtainable by a process comprising a lecithinizing step of reacting a lecithin derivative represented by the following formula (III) with a specific amount of human SOD to obtain a crude PC-SOD and purifying the crude PC-SOD by ions exchange column chromatography.

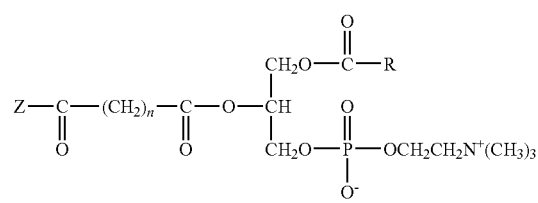

(III)

In the formula (III), R and n are the same as defined for R and n in the formula (I).

Z is a hydroxyl group or an active ester-forming group eliminating a carbonyl group. Examples of the latter include, for example, groups obtained by removing the hydrogen atom from the hydroxyl group in a hydroxyl-containing compound such as p-nitrophenol, 1,3,5-trichlorophenol, pentafluorophenol, 2,4-dinitrophenol, N-hydroxysuccinimide, N-hydroxypiperidine, N-hydroxy-5-norbornene-2,3-dicarboximide, 8-hydroxyquinoline or 2-hydroxypyridine. For synthesis of active esters, known methods (patent document 1, and "Peptide Gousei-no Kiso to Jikken" (Izumiya et al., 1985, published by Maruzen) are available.

[The Lecithinizing Step]

This step is carried out preferably by adding a lecithin derivative solution obtained by dissolving a lecithin derivative represented by the formula (III) in an appropriate solvent to a SOD solution obtained by dissolving human SOD in an appropriate solvent. Specifically speaking, by reacting 1 mol of the lecithin derivative with from 0.05 to 0.4 time, preferably from 0.1 to 0.25 time, as many moles of human SOD, the PC-SOD composition of the present invention can be obtained in high yields.

Control of various reaction conditions such as the addition rate, stirring speed, reaction temperature, reaction time and reaction pressure leads to a higher yield of the PC-SOD composition of the present invention.

The rate at which the lecithin derivative solution is added to the SOD solution is such that the lecithin derivative diffuses throughout the reaction system in a short time, and is usually from 20 to 100 mL/min, preferably from 40 to 80 mL/min.

The reaction speed is such that the lecithin derivative diffuses throughout the reaction system in a short time, and is usually from 50 to 500 rpm, preferably from 100 to 300 rpm.

The upper limit of the reaction temperature is preferably +20° C. because more of the lecithin derivative is introduced into one molecule of SOD as the temperature rises. The lower limit of the reaction temperature is such a temperature that the reaction solutions do not freeze. The reaction temperature is preferably from 0 to +1020 C.

The reaction time is preferably from 0.5 to 72 hours, particularly from 2 to 24 hours.

The reaction pressure is preferably from 0.05 MPa to 0.2 MPa, particularly around atmospheric pressure.

In order to produce the PC-SOD composition of the present invention with more stable quality in high yields, it is preferred to set strict conditions also on the concentration of human SOD in the SOD solution and the way of adding the lecithin derivative.

Specifically, it is preferred to add a lecithin derivative solution obtained by diluting a lecithin derivative with from 20 to 100 times as much of an organic solvent to a SOD solution obtained by diluting human SOD with from 100 to 2000 times as much of an organic solvent.

The solvent to dissolve the SOD may be water or a solvent mixture of water and an organic solvent, preferably a solvent mixture of water and an organic solvent. Such a solvent mixture allows formation of a homogeneous reaction system upon addition of the lecithin derivative solution and prevents formation of precipitates. It is preferred to impart a buffering ability to the solvent by dissolving boric acid or the like.

The water is preferably purified water, ion exchange water, distilled water or water for injection (hereinafter these are comprehensively referred to as "water"). The organic solvent may be isopropyl alcohol, N,N-dimethylformamide, N-methylpyrrolidone, N,N-dimethylacetamide, sulfolane, dimethyl sulfoxide, acetone, 1,4-dioxane, methanol or the like, and is preferably isopropyl alcohol.

The solvent to dilute the lecithin derivative may be one of those mentioned for preparation of the SOD solution and is preferably isopropyl alcohol.

The reaction solution thus obtained (the crude PC-SOD) contains not only the PC-SOD (A), but also the PC-SOD (B), the unreacted human SOD, the unreacted lecithin derivative and other components. As the other components, the unreacted residue(s) of the reagents used for the synthesis of the lecithin derivative may be mentioned.

Then, the crude PC-SOD obtained in the lecithinizing step is purified by ion exchange column chromatography in the purifying step. The purifying step affords the PC-SOD composition of the present invention in high yields.

The purifying step is carried out by charging the crude PC-SOD onto an ion exchange resin packed in a column to allow it to be adsorbed on the resin, and eluting the desired PC-SOD composition with a solvent containing a buffer containing an inorganic salt.

As the ion exchange resin, an anion exchange resin or a cation exchange resin may be used.

The buffer in the elution solvent may be any buffer without any particular restrictions as long as it contains an inorganic salt and has a buffering ability. However, in the case of a phosphate buffer, because the PC-SOD may be insoluble in it, it is necessary to check whether it dissolves the PC-SOD before use. The pH of the buffer is preferably from 6 to 9 in view of the stability of the PC-SOD during purification.

The inorganic salt may be sodium chloride, ammonium sulfate or the like. They may be used singly or in predetermined ratios in a mixture.

The elution solvent preferably contains an organic solvent to dissolve the PC-SOD more easily.

The organic solvent may be isopropyl alcohol, N,N-dimethylformamide, N-methylpyrrolidone, N,N-dimethylacetamide, sulfolane, dimethyl sulfoxide, acetone, 1,4-dioxane, methanol or the like. Among them, methanol is preferred because it dissolves the PC-SOD well and allows efficient purification.

The amount of the organic solvent in the solvent is preferably such that the PC-SOD is soluble and the organic solvent does not retard adsorption of the PC-SOD onto the ion exchange resin. The ratio of the organic solvent is preferably from 10 to 80 vol %, more preferably from 20 to 70 vol %, particularly from 40 to 60 vol %, based on the total volume of the solvent.

The desired PC-SOD is eluted by changing the inorganic salt concentration of the buffer in the solvent.

Specifically speaking, it is preferred to charge the crude PC-SOD on the column, then elute the unabsorbed matters with the following solvent (A), and elute the PC-SOD composition with the following solvent (B).

Solvent (A): a solvent consisting of from 20 to 90 vol % of a buffer (a1) having a pH of from 6 to 9 and an inorganic salt concentration of from 5 to 100 mM and from 10 to 80 vol % of methanol.

Solvent (B): a solvent consisting of from 20 to 90 vol % of a buffer (b1) having a pH of from 6 to 9 and an inorganic salt concentration of from 150 to 400 mM and from 10 to 80 vol % of methanol.

It is preferred to remove the inorganic salt and the organic solvent by ultrafiltration from the fractions containing the PC-SOD composition obtained as mentioned above. After ultrafiltration, an aqueous PC-SOD composition solution containing the PC-SOD composition and water is obtained. Though the PC-SOD composition may be isolated by dehydrating the aqueous solution, it is obtained preferably as an aqueous solution because the PC-SOD composition is usually used in the form of an aqueous solution when formulated into a preparation. The PC-SOD concentration in the aqueous solution is preferably from 0.1 to 300 mg/mL, particularly from 1 to 50 mg/mL.

The PC-SOD composition of the present invention is useful as a drug material and formulated into a preparation through addition of various additives or dissolution.

Its dosage form may be an injection (such as a solution, a suspension, an emulsion or a solid formulation for dissolution before use), a tablet, a capsule, a granule, a powder, a liquid, a liposomal formulation, a gel, a topical powder, a spray, a powder inhalant or a suppository.

It may be administered by injection (intramuscular, subcutaneous, intradermal or intravenous), orally or by inhalation. Its dose is determined on a case-by-case basis, depending on the drug preparation method, dosage form, the type of the disease, the route of administration, regimen, purpose and the weight of the patient, and may, for example, from 0.5 to 200 mg per day for an adult.

EXAMPLES

Now, the present invention will be described by referring to Examples. However, the present invention is by no means restricted to those specific Examples.

Example 1

Preparation of PC-SOD Composition

Distilled water for injection (manufactured by Otsuka Pharmaceutical Co., Ltd., product name: Otsuka Distilled Water) (9000 mL) was poured into a 20 L flask, and boric acid (27.7 g), NaOH (3.6 g) and KCl (33.7 g) were added and dissolved successively. Then, SOD in water (100 g, SOD concentration 113.6 mg/mL) was added, and isopropyl alcohol (2000 mL) cooled to 8° C. in a chromatography chamber was added dropwise at a rate of 33 mL/min with stirring at 210 rpm to give a SOD solution.

A lecithin derivative shown below (15.7 g) prepared in accordance with Japanese Patent 3070980 was dissolved in isopropyl alcohol (500 mL) and filtered through a hydrophobic filter to remove the insolubles. Isopropyl alcohol was added to the filtrate up to a total volume of 8000 mL to give a lecithin derivative solution. The temperature of the solution was 8° C. Then, the lecithin derivative solution (8000 mL) was added dropwise to the SOD solution at a rate of 66 mL/min and stirred at 210 rpm for 4 hours to give a reaction solution.

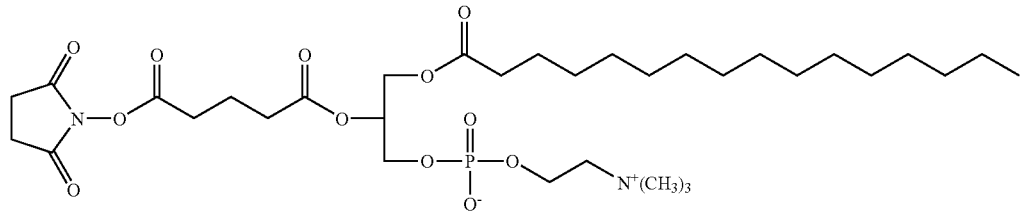

All the reaction solution was charged onto a column packed with an ion exchange resin (Cellulofine sf A-500) preliminarily equilibrated with a 1:1 (volume ratio) liquid mixture of borate buffer (50 mmol/L, pH 8.5±0.2) and methanol, and the unabsorbed matters were eluted with the liquid mixture to give fractions containing N-hydroxysuccinimide, 1H-tetrazole and dicyclohexylcarbodiimide.

Then, the unmodified SOD was eluted with a 1:1 mixture of 50 mmol/L borate buffer (pH 8.5±0.2, NaCl concentration=25 mmol/L) and methanol as an elution solvent.

Subsequent elution with a 1:1 mixture of 50 mmol/L borate buffer (pH 8.5±0.2, NaCl concentration=200 mmol/L) and methanol as an elution solvent gave a fraction containing the PC-SOD composition.

The fraction containing the PC-SOD composition was ultrafiltered through an ultrafilter PLGC0005 (nominal molecular weight limit 10,000, filtration area 0.5 m$^2$) manufactured by Millipore Corporation for desalting, replacement of methanol with distilled water for injection and concentration adjustment, until the electric conductivity of the filtrate became the same as that of the distilled water for injection.

The PC-SOD concentration was adjusted to about 40 mg/mL to give a PC-SOD composition aqueous solution (Lot.001). All the procedures so far were carried out in a chromatography chamber maintained at 4° C. with solution temperature monitoring.

The PC-SOD composition was fractionated by preparative HPLC through a HPLC column, Phenyl 5PW-RP (75 mm×4.6 mm, Tosoh Corporation) using a mobile phase with a concentration gradient from an aqueous solution containing 0.1% trifluoroacetic acid and 20% acetonitrile to an aqueous solution containing 0.075% trifluoroacetic acid and 90% acetonitrile running at a rate 0.8 mL/min, and fractions corresponding to respective PC-SODs were collected. As the detector, a UV detector (wavelength 220 nm) was used, and the column temperature was room temperature.

The collected fractions were analyzed by MALDI TOF-MS to determine the molecular weights and identify the fragments. The numbers (m) of lecithin derivatives in 1 molecule of PC-SODs, the ratios (molar ratios) of PC-SODs with different m's, the average of m, and the average of m in PC-SOD dimers are shown below in Table 1.

The aqueous solution (Lot.001) contained PC-SODs having from 1 to 4 molecules of the lecithin derivatives, and the average of m was 2.

Examples 2 and 3

The procedures in Example 1 were followed to give PC-SOD composition aqueous solutions (Lots. 002 and 003). The numbers (m) of lecithin derivatives in 1 molecule of PC-SODs, the ratios (molar ratios) of PC-SODs with different m's, the average of m, and the average of m in PC-SOD dimers for each solution are shown collectively below in Table 1.

TABLE 1

|  | Ex. 1: Lot. 001 | Ex. 2: Lot. 002 | Ex. 3: Lot. 003 |
| --- | --- | --- | --- |
| m = 1 | 31 mol % | 31 mol % | 32 mol % |
| m = 2 | 43 mol % | 43 mol % | 43 mol % |
| m = 3 | 16 mol % | 16 mol % | 15 mol % |
| m = 4 | 10 mol % | 10 mol % | 10 mol % |
| Average of m | 2 | 2 | 2 |
| Average of m in dimers | 4 | 4 | 4 |

Example 4

Purity Assay by HPLC (Part 1)

The aqueous solution obtained in Example 1 (Lot 001, 500 µL) was diluted with distilled water for injection to a PC-SOD concentration of 30 mg/mL, and a portion (500 μL) of the diluted solution mixed with distilled water for injection (2500 μL) to give an assay sample. HPLC analysis of the assay sample revealed that the ratio of the PC-SOD (A) to the total of PC-SODs was 96.7% (in terms of peak area in the chromatogram).

For the HPLC analysis, a mobile phase with a concentration gradient from an aqueous solution containing 0.1% trifluoroacetic acid and 20% acetonitrile to an aqueous solution containing 0.075% trifluoroacetic acid and 90% acetonitrile was run at a rate of 0.8 mL/min through a column YMC A-502 S-5 120A CN (150 mm×4.6 mm, manufactured by YMC) at a column temperature of room temperature, and a UV detector (wavelength 220 nm) was used as the detector.

Example 5

Purity Assay by HPLC (Part 2)

A PC-SOD aqueous solution (Lot. 005) was prepared in the same manner as in Example 1, and it was analyzed by HPLC in the same manner as in Example 4. The ratio of the PC-SOD (A) to the total of PC-SODs was 97.3% (in terms of peak area in the chromatogram).

Example 6

Purity Assay by Sodium Dodecyl Sulfate Polyacrylamide Gel Electrophoresis

The aqueous solution obtained in Example 1 (Lot 001, 500 μL) was diluted with distilled water for injection to a PC-SOD concentration of 30 mg/mL, and a portion (100 μL) of the diluted solution was mixed with water (2900 μL) to give a sample solution.

A mixture of the sample solution (100 μL) and water (900 μL) was used as a control solution.

20 μL aliquots of the sample solution and the control solution were heated with a sample buffer (8 μL) at 95° C. for 3 minutes. The sample buffer was prepared by dissolving glycerine (10 g), sodium dodecyl sulfate (2 g) and bromophenol blue (100 mg) in tris-HCl buffer (50 mmol/L) to make a solution having a total volume of 100 mL and adding 2-mercaptoethanol (5 μL) to a 95 μL aliquot of 100 mL of the solution.

4 μL of the sample solution and control solution treated above were electrophoresed, and immediately after the electrophoresis, the gel was stained in a staining chamber. After the staining, the gel was soaked in a protective solution prepared by adding water to glycerin (20 mL) up to a total volume of 500 mL, and dried.

From the comparison between the minor bands from the sample solution and the major band from the control solution, it was found that the ratio of the PC-SOD (A) in the PC-SOD composition was at least 90% (in terms of peak area of the chromatogram).

Example 7

Assay of Specific Activity

Specific assay was measured by the cytochrome C method as described by Y. Oyanagi ((SOD and active oxygen regulators, p.95(1989), J. M. McCord (J. Biol. Chem., Vol.224, p.6049(1969) and K. Asada (Agr. Biol. Chem., Vol.38, p.471 (1974)). Human SOD having a specific activity within the range of from 4500 to 5500 was used as the standard.

From the PC-SOD compositions in the previous Examples, samples with various concentrations were prepared, and a xanthine oxidase solution was added. The UV absorbances (550 nm) were measured. The specific activities of the samples were determined from a calibration curve obtained from the concentration and absorbance measurements by the least-squares method. The specific activity of the PC-SOD composition in Lot. 001 was 3400 (U/mg-SOD). Specific activity in the unit, "U/mg-SOD", refers to that of the total SODs (1 mg).

Example 8

Fatty Acid Assay

Palmitic acid (256 mg) was dissolved in ethanol to make 20 mL of a 50 mmol/L standard stock solution. The standard stock solution was diluted with ethanol to give 0.1 mmol/L, 0.05 mmol/L and 0.01 mmol/L palmitic acid standard samples. The value, (the weight of palmitic acid)/(the molecular weight of palmitic acid=256.43) was defined as Factor ($F^p$).

Margaric acid (27 mg) was dissolved in ethanol to give 200 mL of a 0.5 mmol/L internal standard solution.

The internal standard solution (100 μL) was added to the palmitic acid standard samples (100 μL), the aqueous solution (100 μL) obtained in Example (Lot. 001) and the aqueous solutions (100 μL respectively) obtained in the same manner as in Example 1 (Lot. 005 and Lot. 008), respectively. As the blank, ethanol (100 μL) was used.

Each sample was stirred with Liquid A and Liquid B of a long chain- and short chain- fatty acid labeling reagent (manufactured by YMC) composed of Liquid A, Liquid B and Liquid C in a thermostatic bath at 60° C. for 20 minutes. After addition of Liquid C (200 μL), the samples were stirred in a thermostatic bath at 60° C. for 15 minutes to give HPLC samples.

HPLC was carried out by passing a mobile phase with a concentration gradient from an aqueous solution containing 0.01% trifluoroacetic acid and 20% acetonitrile to an aqueous solution containing 0.01% trifluoroacetic acid and 90% acetonitrile at a rate of 1 mL/min through a column YMC A-512 S-5 120A CN (150 mm×6.0 mm, manufactured by YMC) at a column temperature of room temperature. A UV detector (wavelength 230 nm) was used as the detector.

The peak areas % for palmitic acid were determined from the resulting HPLC chromatograms and compared with those for the internal standard solution to determine the amounts of palmitic acid. The palmitic acid concentration per total of PC-SODs was 0.074 mmol/mg in Lot.001, 0.094 mmol/mg in Lot. 005, and 0.067 mmol/mg in Lot. 008.

INDUSTRIAL APPLICABILITY

The PC-SOD composition of the present invention is an excellent composition which has stable enzymatic activity and good in vivo stability and is easy to formulate into a preparation. Therefore, it is useful for various therapeutic agents such as an antirheumatic drug and therapeutic agents for autoimmune diseases.

The entire disclosure of Japanese Patent Application No. 2004-297519 filed on Oct. 12, 2004 including specification, claims and summary is incorporated herein by reference in its entirety.

What is claimed is:

1. A lecithinized human superoxide dismutase composition comprising a lecithinized human superoxide dismutase A and a lecithinized human superoxide dismutase B, wherein each lecithinized human superoxide dismutase has at least one amino group in a copper-and/or zinc-coordinated human superoxide dismutase substituted by a hydroxyethylthio group at the cysteine at position 111, and each lecithinized human superoxide dismutase has at least one lecithin moiety represented by the following formula (I):

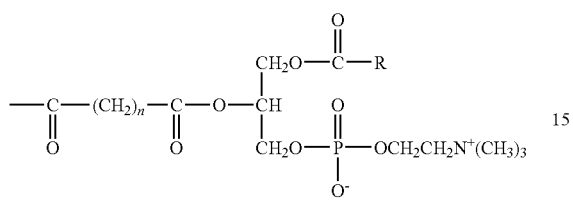

(I)

wherein R is a $C_{8-30}$ alkyl group, and n is an integer of from 2 to 10, wherein the lecithinized human superoxide dismutase (A) has m number of amino groups substituted with the lecithin moieties wherein m is an integer of from 1 to 4, and the lecithinized human superoxide dismutase (A) consists of from 25 to 40 mol % of a lecithinized superoxide dismutase (a1) wherein m=1, from 35 to 50 mol % of a lecithinized superoxide dismutase (a2) wherein m=2, from 10 to 20 mol % of a lecithinized superoxide dismutase (a3) wherein m=3 and from 5 to 15 mol % of a lecithinized superoxide dismutase (a4) wherein m=4, and wherein the lecithinized human superoxide dismutase B has 5-12 amino groups substituted with lecithin moieties represented by the formula (I).

2. The lecithinized human superoxide dismutase composition according to claim 1, wherein the ratio of the lecithinized human superoxide dismutase (A) to the total of lecithinized human superoxide dismutases A and B measured by high performance liquid chromatography, in terms of peak area in the chromatogram, is at least 85%.

3. The lecithinized human superoxide dismutase composition according to claim 1, wherein the ratio of the lecithinized human superoxide dismutase (A) to the total of lecithinized human superoxide dismutases A and B measured by sodium dodecyl sulfate-polyacrylamide gel electrophoresis, in terms of peak area in the chromatogram, is at least 80%.

4. The lecithinized human superoxide dismutase composition according to claim 1, which has a specific activity of at least 2000 units per 1 mg of the total of lecithinized human superoxide.

5. The lecithinized human superoxide dismutase composition according to claim 1, further comprising from 0.01 to 0.15 nmol of a fatty acid represented by the formula (II) per 1 mg of the total of lecithinized human superoxide dismutases: RCOOH (II), wherein R is a $C_{8-30}$ alkyl group.

6. The lecithinized human superoxide dismutase composition according to claim 1, which contains the lecithinized superoxide dismutase (A) in the form of a dimer of lecithinized superoxide dismutases which are the same or different in m.

7. A process for producing the lecithinized human superoxide dismutase composition as defined in claim 1, which comprises a lecithinizing step of reacting a lecithin derivative represented by the following formula (III):

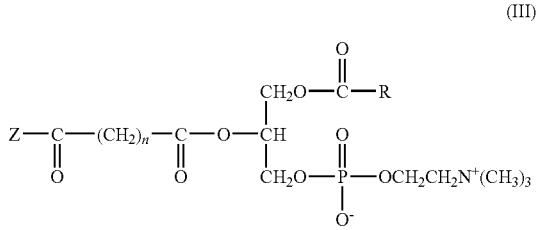

(III)

wherein R is a $C_{8-30}$ alkyl group, Z is a hydroxyl group or an active ester-forming group, and n is an integer of from 2 to 10 with from 0.05 to 0.4 times as many moles of copper-and/or zinc-coordinated human superoxide dismutase substituted by a hydroxyethylthio group at the cysteine at position 111 to obtain a crude lecithinized human superoxide dismutase, and purifying step the crude lecithinized human superoxide dismutase by ion exchange column chromatography.

8. The process according to claim 7, wherein the purifying step is carried out by allowing the crude lecithinized human superoxide dismutase obtained in the lecithinizing step to be adsorbed on an ion exchange resin, then eluting the unreacted lecithinized human superoxide dismutase with the following solvent (A), and eluting the lecithinized human superoxide dismutase composition with the following solvent (B):

solvent (A): a solvent consisting of from 20 to 90 vol % of a buffer (a1) having a pH of from 6 to 9 and an inorganic salt concentration of from 5 to 100 mM and from 10 to 80 vol % of methanol:

solvent (B): a solvent consisting of from 20 to 90 vol % of a buffer (b1) having a pH of from 6 to 9 and an inorganic salt concentration of from 150 to 400 mM and from 10 to 80 vol % of methanol.

\* \* \* \* \*